(12) United States Patent
Trivedi et al.

(10) Patent No.: US 8,894,977 B2
(45) Date of Patent: Nov. 25, 2014

(54) ORAL TREATMENT COMPOSITIONS CONTAINING AN ANTI-ADHESION AGENT, ANTIBACTERIAL AGENT AND INCOMPATIBLE COMPOUND

(75) Inventors: Harsh M. Trivedi, Somerset, NJ (US); Tao Xu, East Brunswick, NJ (US); Ramachandra Shastry, Dayton, NJ (US); James Masters, Ringoes, NJ (US); André Michelle Morgan, Robbinsville, NJ (US)

(73) Assignee: Colgate-Palmolive Company, New York, NY (US)

( * ) Notice: Subject to any disclaimer, the term of this patent is extended or adjusted under 35 U.S.C. 154(b) by 1239 days.

(21) Appl. No.: 11/239,490

(22) Filed: Sep. 29, 2005

(65) Prior Publication Data

US 2006/0134017 A1 Jun. 22, 2006

Related U.S. Application Data

(60) Provisional application No. 60/636,786, filed on Dec. 16, 2004.

(51) Int. Cl.
*A61K 8/66* (2006.01)
*A61Q 11/00* (2006.01)
*A61K 38/48* (2006.01)
*A61K 45/06* (2006.01)
*A61K 31/14* (2006.01)
*A61K 45/00* (2006.01)

(52) U.S. Cl.
CPC .......... *A61K 31/14* (2013.01); *C12Y 304/22002* (2013.01); *A61K 38/4873* (2013.01); *A61K 45/06* (2013.01); *A61K 45/00* (2013.01)
USPC .............................................. 424/50; 424/49

(58) Field of Classification Search
USPC .......................................................... 424/50
See application file for complete search history.

(56) References Cited

U.S. PATENT DOCUMENTS

| | | | |
|---|---|---|---|
| 3,194,738 A | 7/1965 | Harrisson et al. | |
| 4,071,614 A * | 1/1978 | Grimm, III | 424/49 |
| 4,082,841 A | 4/1978 | Pader | |
| 5,368,844 A * | 11/1994 | Gaffar et al. | 424/49 |
| 5,370,864 A | 12/1994 | Peterson et al. | |
| 5,670,142 A | 9/1997 | Rubin et al. | |
| 5,776,435 A | 7/1998 | Gaffar et al. | |
| 6,241,973 B1 | 6/2001 | Rinne | |
| 6,290,933 B1 | 9/2001 | Durga et al. | |
| 6,379,654 B1 | 4/2002 | Gebreselassie et al. | |
| 6,447,758 B1 * | 9/2002 | Carale et al. | 424/54 |
| 6,652,841 B1 * | 11/2003 | Brown et al. | 424/49 |
| 6,692,726 B1 | 2/2004 | Morgan et al. | |
| 6,740,311 B2 | 5/2004 | White, Jr. et al. | |
| 2003/0206874 A1 | 11/2003 | Doyle et al. | |
| 2003/0211053 A1 * | 11/2003 | Szeles et al. | 424/50 |
| 2003/0211054 A1 * | 11/2003 | Szeles et al. | 424/50 |
| 2004/0042977 A1 | 3/2004 | Williams et al. | |
| 2004/0156796 A1 | 8/2004 | Morgan et al. | |

FOREIGN PATENT DOCUMENTS

| | | |
|---|---|---|
| CA | 959764 | 12/1974 |
| FR | 2036 | 12/1963 |
| JP | 63215668 | 9/1988 |
| JP | 10077276 | 3/1998 |
| WO | 9324142 | 12/1993 |
| WO | WO 9324142 A1 * | 12/1993 |
| WO | WO03/094877 | 11/2003 |
| WO | WO 2004/019898 | 3/2004 |
| WO | WO2004/100913 | 11/2004 |

OTHER PUBLICATIONS

BASF—Product Information BASF Chemicals NAFTA—Pluronic. [online]. 2013. [retrieved on Sep. 30, 2013]. Retrieved from the Internet: <URL:http://worldaccount.basf.com/wa/NAFTA~en_US/Catalog/ChemicalsNAFTA/pi/BASF/Brand/pluronic>. 2 pages.*
Hellgren, L et al. "Peptide hydrolases from antarctic krill—an important new tool with a promising medical potential." in: Margesin, R et al., Biotechnological Applications of Cold-Adapted Organisms (Austria, Springer-Verlag Berlin Heidelberg, 1999), pp. 63-74.*
Sertoli, A et al. Tegobetaine in contact lens solutions. Contact Dermatitis. 1987. 16(2): 111-112.*
Kabanov, AV et al. Pluronic block copolymers: novel functional molecules for gene therapy. Advanced Drug Delivery Reviews. 2002. 54: 223-233.*
Froning et al. "Characteristics of bone . . . " Poultry Science, vol. 60, 1981, pp. 1443-1447.
Berg et al., 2001, "Proteolytic degradation of oral biofilms in vitro and in vivo: potential of proteases originating from *Euphausia superba* for plaque control," European J. Oral Sciences 109(5):316-324, Abstract only.
Mukherjee "Study of anticalculus agents" Journal of Periodontal Research (1969) 4:1 pp. 26-35 Abstract.
Miller et al. "Enzyme separation techniques for the study of growth of cells from layers of bovine dental pulp" Inn Vitro (1976) 12:8 pp. 580-588 Abstract.
Quesnel L.B., et al. "Synergism between chlorhexidine and sulphadiazine" Journal of Applied Bacteriology (1978) 45:397-405.
Shea, Catherine & Williamson. J. Chad "Rapid Analysis of Bacterial Adhesion in a Microplate Assay" Biotechniques, (1990) 8:9.
Herles, S. et al. "Chemostat flow cell system: an in vitro model for the evaluation of antiplaque agents" J Dent Res 73:11 pp. 1748-1755, 1994.

\* cited by examiner

*Primary Examiner* — Allison Fox
*Assistant Examiner* — Susan E Fernandez
(74) *Attorney, Agent, or Firm* — Howard C. Lee

(57) ABSTRACT

The present invention encompasses an oral treatment composition containing an anti-adhesion agent, preferably a cysteine protease and most preferably ficin. In another aspect, the cysteine protease is in combination with one or more ingredients, such as antibacterial agent and surfactant. The anti-adhesion agent mitigates interaction between a subject oral cavity and plaque-forming materials.

17 Claims, No Drawings

ORAL TREATMENT COMPOSITIONS CONTAINING AN ANTI-ADHESION AGENT, ANTIBACTERIAL AGENT AND INCOMPATIBLE COMPOUND

CROSS REFERENCE TO RELATED APPLICATION

This application claims priority to U.S. Provisional Patent Application Ser. No. 60/636,786, filed 16 Dec. 2004, the contents of which are incorporated herein by reference.

BACKGROUND OF THE INVENTION

Dental plaque or plaque bio-film is a soft deposit that forms on surfaces of the oral cavity, such as tissue and teeth, and is comprised of an accumulation of bacteria and salivary as well as food by-products. Plaque adheres tenaciously at the points of irregularity or discontinuity (e.g., on rough calculus surfaces, at the gum line, on tongue surface and within crevices, and the like). Besides being unsightly, plaque is implicated in the occurrence of gingivitis and other forms of periodontal disease.

Bacteria are present on the tongue. The bacteria are a part of a protective bio-film that essentially renders them resistant to most treatments. Few people clean their tongue after brushing, even though it's been shown that as much as 50 percent of the mouth's bacteria can be found here. Additionally, for many people, brushing or scraping the tongue is difficult because of the gag reflex. Therefore, cleaning the tongue non-mechanically is highly desirable for those who are unable to do so with a mechanical device.

In spite of the extensive prior art relating to antibacterial dentifrice and oral treatment compositions, there is still a need in the art to formulate a product capable of enhanced effect in the retardation of bacterial plaque accumulation.

BRIEF SUMMARY OF THE INVENTION

The present invention encompasses an oral treatment composition containing an anti-adhesion agent, preferably a cysteine protease and most preferably ficin. In another aspect, the cysteine protease is in combination with one or more ingredients, such as antibacterial agent and surfactant. The anti-adhesion agent mitigates interaction between a subject oral cavity and plaque-forming materials.

In a further feature, a compound relatively incompatible with the anti-adhesion agent and/or the antibacterial agent is included in a limited amount and is controlled to minimize decline or degradation of activity of the anti-adhesion agent and/or the antibacterial agent. In a still further feature, a relatively incompatible compound is included and segregation is implemented to prevent or inhibit contact with the anti-adhesion agent and/or antibacterial agent.

DETAILED DESCRIPTION OF THE INVENTION

In one aspect of the present invention, the oral treatment composition contains an effective amount of an anti-adhesion protease enzyme. In another aspect, the oral treatment composition is formulated using a vehicle containing an effective amount of the anti-adhesion protease enzyme or mixture of such protease enzyme.

The enzymes of the present invention inhibit build-up of bacterial layer that would result in plaque build-up. Such enzymes of the invention attach to and anchor to oral surfaces, including tissue, and, thus, inhibit the growth of plaque or its further growth. The terms "anti-adhesion" and "anti-attachment" are used herein interchangeably. The selected enzymes of the invention are anti-adhesion protease enzymes, desirably cysteine protease and are most desirably selected from the group ficin, papain and krillase. Preferably, the anti-adhesion agent comprises ficin and one or more other enzymes, such as other anti-adhesion enzyme(s) or another type of enzyme, such as bromelain, chymotrypsin, alcalase, amalysecs, glucose oxidase, cellusases, lipsases, and/or other protease besides the anti-adhesion cysteine protease.

Ficin for use in the invention may be by drying and filtering the latex from the *Ficus* genus, for example *Ficus glabrata*. Papain for use in the invention may be obtained from the fruit and leaves of *Carica papaya*. Krillase for use in the invention may be extracted from antarctic krill (*Euphausia superba*).

In another embodiment, the composition comprises an orally acceptable antiplaque, including plaque disrupting and anti-adhesion agents and combinations thereof.

The amount of anti-adhesion agent present in the composition depends on the application for use. It is present at less than 100 parts by weight in a composition or in a suitable vehicle. The anti-adhesion agent is desirably present in an amount by weight of at least 0.01 parts per 100 parts of the composition. In a broad aspect, the anti-adhesion enzyme agent is present in an amount by weight of about 0.01 to about 10 parts by weight for every 100 parts by weight of total composition. More desirably it is at least 0.05 parts; and preferably 0.03 to 0.30 parts suitable for a paste composition.

One or more other antiplaque agents can be present in an antiplaque effective total amount. Suitable agents include without limitation stannous, copper, magnesium and strontium salts, dimethicone copolyols such as cetyl dimethicone copolyol, glucoamylase, glucose oxidase, urea, calcium lactate, calcium glycerophosphate, strontium polyacrylates and chelating agents such as citric and tartaric acids and alkali metal salts thereof.

One selected enzyme that may be formulated in combination with a protease enzyme is the glucoamylase. Other enzymes that may be used in the practice of the present invention include other carbohydrases such as alpha-amylase, beta-amylase, dextranase and mutanase and lipases such as plant lipase, gastric lipase, pancreatic lipase, pectinase, tannase lysozyme and serine proteases.

Other suitable enzymes that can comprise the present invention include lysozyme, derived from egg white, which contains a single polypeptide chain crosslinked by four disulfide bonds having a molecular weight of 14,600 daltons. The enzyme can exhibit antibacterial properties by facilitating the hydrolysis of bacterial cell walls cleaving the glycosidic bond between carbon number 1 of N-acetylmuramic acid and carbon number 4 of N-acetyl-D-glucosamine, which in vivo, these two carbohydrates are polymerized to form the cell wall polysaccharide. Additionally, pectinase, an enzyme that is present in most plants, facilitates the hydrolysis of the polysaccharide pectin into sugars and galacturonic acid.

Antibacterial agents useful in the practice of the present invention include all known, such as nonionic and cationic agents. Particularly useful are quaternary ammonium and related compounds. Suitable compounds include benzethonium chloride, or diisobutylphenoxyethoxyethyl dimethyl benzyl ammonium chloride, and cetyl pyridinium chloride.

Other cationic antibacterial quaternary ammonium compounds useful and desirable in the practice of the present invention include those in which one or two of the substituents on the quaternary nitrogen has a carbon chain length (typically alkyl group) of some 8 to 20, typically 10 to 18, carbon atoms while the remaining substituents have a lower number of carbon atoms (typically alkyl or benzyl group), such as 1 to 7 carbon atoms, typically methyl or ethyl groups. Dodecyl trimethyl ammonium bromide, benzyl dimethyl stearyl ammonium chloride, cetyl pyridinium chloride (CPC) and quaternized 5-amino-1,3-bis(2-ethylhexyl)-5-methyl hexa hydro-pyrimidine are typical quaternary ammonium antibacterial agents. The invention contemplates preferred pyridinium components, such as cetyl (C-16), stearyl (C-18) and myristyl (C-18) pyridinium and salts of same formed with halide or another anion. A further illustrative list of useful antibacterial agents is provided in U.S. Pat. No. 5,776,435 to Gaffar et al., incorporated herein by reference.

Abrasives preferred for use the practice of the present invention include silica materials and particularly silica gels and precipitated amorphous silica having an oil absorption value of less than 100 cc/100 g silica and preferably in the range of from about 45 cc/100 g to less than about 70 cc/100 g silica.

The composition may include a vehicle or paste preferably comprises a water-phase, containing a humectant therein. The humectant is preferably glycerin, sorbitol, xylitol, and/or propylene glycol of molecular weight in the range of 200 to 1,000; but other humectants and mixtures thereof may also be employed. The humectant concentration typically totals about 5 to about 70% by weight of the oral composition.

The oral treatment compositions of the present invention can contain a variety of optional ingredients. As described below, such optional ingredients can include, but are not limited to, thickening agents, surfactants, a source of fluoride ions, a synthetic anionic polycarboxylate, a flavoring agent, antitartar agents, and coloring agents.

The dentifrice composition of the present invention may also contain ingredients that stabilize enzymes in a dentifrice environment. These stabilizers protect the enzyme from inactivation by chelating metal impurities present in the dentifrice composition which have the propensity to denature the active site of the enzyme by protecting the enzyme from oxidation. Chelating agents include ethylene diamine tetraacetic acid (EDTA) and sodium gluconate at concentrations between 0.01 and 1%, preferably between 0.1 and 0.5%. Agents stabilizing the enzyme against oxidation include sodium bisulfite, metal gallates, sodium stannate and ascorbic acid at concentrations between about 0.03 and about 2.0%, preferably between about 0.1 and about 0.75%.

Synthetic anionic polycarboxylates may also be used in the dentifrice compositions of the present invention as an efficacy enhancing agent for any antibacterial, antitartar or other active agent within the dentifrice composition. Such anionic polycarboxylates are generally employed in the form of their free acids or preferably partially or more preferably fully neutralized water soluble alkali metal (e.g., potassium and preferably sodium) or ammonium salts. Preferred are 1:4 to 4:1 copolymers of maleic anhydride or acid with another polymerizable ethylenically unsaturated monomer, preferably methylvinylether/maleic anhydride having a molecular weight (M.W.) of about 30,000 to about 1,800,000 and most preferably about 30,000 to about 700,000. Examples of these copolymers are available from GAF Corporation under the tradename Gantrez (e.g., AN 139 (M.W. 500,000), AN 119 (M.W. 250,000); S-97 Pharmaceutical Grade (M.W. 700,000), AN 169 (M.W. 1,200,000-1,800,000), and AN 179 (M.W. above 1,800,000)), wherein the preferred copolymer is S-97 Pharmaceutical Grade (M.W. 700,000).

When present, the anionic polycarboxylate is employed in amounts effective to achieve the desired enhancement of the efficacy of any antibacterial, antitartar or other active agent within the oral treatment composition. Generally, the anionic polycarboxylates is present within an exemplary toothpaste form of the oral treatment composition from about 0.05% to about 4% by weight, preferably from about 0.5% to about 2.5% by weight.

Various other materials may be incorporated in the oral treatment compositions of this invention, including desensitizers (such as potassium nitrate), whitening agents, preservatives, silicones, and chlorophyll compounds. These additives, when present, are incorporated in the oral treatment composition in amounts that do not substantially adversely affect the properties and characteristics desired.

EXAMPLE I

Dentifrice Formulation Containing Anti-adhesion Enzyme

Enzymes are formulated in a silica base formulation. Table 1 gives the exemplary dentifrice formulations. All values are weight percentages, unless otherwise indicated. Key formula ingredients of the formulation are enzymes, ficin, papain and krillase at 0.226% by weight, a mixed silica abrasive system for superior cleaning of 25% by weight, and a mixed surfactant system of 0.5% SLS/1.5% pluronic and 1% betaine, each by weight. A peppermint-spearmint flavor that is stable with enzymes is also included. The compositions are each selected to deliver attributes (such as foam, flavor, mouth feel and aesthetics) without compromising activity of enzymes. For the enzyme concentration, a dose response study targeted to select effective levels of enzymes was carried out prior to selecting the clinical formulations. Based on the in vitro studies, the clinical products were made in the OPTC (Oral Process Technology Center) under GMP conditions.

TABLE 1

Formulations of dentifrice containing enzymes

| INGREDIENT | Ficin | Papain | Krillase |
|---|---|---|---|
| 70% Sorbitol | 24.374 | 24.374 | 24.374 |
| 99.5% Synthetic Glycerin - USP | 20.0 | 20.0 | 20.0 |
| Purified Water | 17.0 | 17.0 | 17.0 |
| Dental Type Silica (Sylodent XWA 650 - USP) | 17.0 | 17.0 | 17.0 |
| Dental Type Silica (Zeodent 115) | 8.000 | 8.000 | 8.000 |
| Polyethylene Glycol 600 (PEG-12) NF | 3.000 | 3.000 | 3.000 |
| No. 2 Synthetic Amorph. Precipitated Silica - Zeodent 165 | 2.500 | 2.500 | 2.500 |
| 29% Sodium Lauryl Sulfate | 0.5 | 0.5 | 0.5 |
| Poloxomer 407 | 1.500 | 1.500 | 1.500 |
| Sodium CMC 2000S - 12 USP | 1.200 | 1.200 | 1.200 |
| Natural and artificial mixed spearmint | 1.100 | 1.100 | 1.100 |
| 30% Cocamidopropyl Betaine | 1.000 | 1.000 | 1.000 |
| Sodium Monofluorophosphate - USP | 0.760 | 0.760 | 0.760 |
| Tetrasodium Pyrophosphate - Fine (FCC) | 0.500 | 0.500 | 0.500 |
| Sodium Saccharin USP | 0.500 | 0.500 | 0.500 |
| Xanthan Gum - NF | 0.400 | 0.400 | 0.400 |
| Poly OXWSR-N 750 | 0.100 | 0.100 | 0.100 |
| Blue Poly 50 | 0.300 | 0.300 | 0.300 |
| Blue color solution | 0.040 | 0.040 | 0.040 |
| Ficin | 0.226 | 0 | 0 |
| Papain | 0 | 0.226 | 0 |
| Krillase | 0 | 0 | 0.226 |
| TOTAL | 100 | 100 | 100 |

EXAMPLE II

Characterization of Enzymes

Total Protein Concentration

Total protein content was determined using a non interfering total protein concentration assay from Genotech. The total protein concentration of the krillase powder is about 30-40%, and 60-70% for EDC (Enzyme Development Corporation) papain and about 90% or greater protein concentration for ficin.

Activity Assay

The activity of proteases was evaluated using generic protease assay from Panvera at 40° C. and neutral pH. The activity was assessed relative to papain on an equal weight basis of neat powder samples. Krillase protease enzymes are a mixture of eight different proteases; thus, the activity of any one of the eight was not discernable by the present assay. The assay aided in determining dose for the dose response studies. In clinical formulations, enzymes were dosed based on an equal weight basis. Table 2 gives the relative activity of neat enzymes.

TABLE 2

| Activity various enzymes by protease assay | |
|---|---|
| Enzyme | Activity CPU/g (+/−3) |
| Ficin | 23 |
| Papain | 25 |
| Krillase | 47 |

EXAMPLE III

Anti-attachment Efficacy Study—Artificial Mouth

To test the efficacy of the actives in toothpaste formulas, the Artificial Mouth model was utilized. This is generally described in Herles, S., S. Olsen, et al. (1994). "Chemostat flow cell system: an in vitro model for the evaluation of antiplaque agents." *J Dent Res* 73(11): 1748-55. The Artificial Mouth model is a flow system that simulates the human mouth. Saliva-coated hydropxyapatite (SHAP) disks served as the artificial teeth, and a bacteria culture consisting of the main oral bacteria in humans flowed through the system at a speed consistent with the in vivo human saliva. Eight disks for each treatment were then placed in the chemostat flow cell and oral bacteria culture was allowed to flow through the disks overnight (20-24 hours) to see if actives coated on the disk surfaces would prevent bio-film formation. After 24 hours the SHAP disks were removed and amount of bacteria quantified. The $ABS_{610}$ of the solutions were then measured and analyzed. This result gave an estimate of the amount of bacteria that were adhering on the SHAP disks. From this value, the percentage anti-adhesion effectiveness of the pastes is evaluated relative to a matching negative control. Two concentrations of protease were tested for each of the three protease; namely. 0.226 weight percent and 0.065 weight percent. The artificial mouth anti-adhesion experiment suggests that at the two concentrations tested for each of the three proteases, on average, all three had efficacy above that of the negative control pastes, which did not contain any of the enzyme. However, based on statistical analysis, the efficacy of krillase was not demonstrated. Papain and ficin showed efficacy at 0.226% concentration. Ficin showed similar efficacy at 0.065% and 0.226%. Based on these results, GMP batches for proof of concept clinical studies were prepared. The in vitro results showed that ficin was better then the papain, which was in turn better then the matching placebo paste.

EXAMPLE IV

In Vivo Clinical Evaluation

Two human clinical studies were conducted to test the anti-adhesion efficacy of the products relative to matching negative control paste. The clinical procedure for measurement of anti-adhesion efficacy with the end benefit of reduced plaque is indicated below.

A. Modified Gingival Margin Plaque Index Determination (MGMPI)—Test Products 0.226% Ficin and Matching Negative Control Fifteen (15) in-house panelists were recruited and enrolled in this clinical study. Fourteen (14) panelists completed this three-week study. One panelist was dropped from the study due to minor illness that required antibiotic use. Panelists reported to the dental clinic for an oral examination and review of medical history. All acceptable panelists received a prophylaxis (dental cleaning) and started a one-week washout with Colgate Great Regular. During the treatment phase of the clinical study, the panelists reported to the dental clinic on their assigned morning. They received a full scaling and prophylaxis to remove all dental calculus and plaque. Disclosing solution was used during the procedure to verify complete removal of all plaque and calculus. Panelists then used 1.5 gm of the assigned dentifrice and then brushed for 60 seconds followed by rinse for 5 seconds with 10 ml of water. They were then instructed to refrain from all oral hygiene for 24 hours at the end of which they returned to the dental clinic rinsed with disclosing solution and had their plaque scored. Upon completion of the plaque score the panelists resumed normal oral hygiene (brushing whole mouth two times per day) using the washout product. Results are shown below.

| Plaque score (MGMPI) | Enzyme toothpaste (0.226% Ficin) | Matching Placebo toothpaste |
|---|---|---|
| Mean 24 hr. score | 14.55 ± 8.50* | 30.38 ± 17.99 |

*Statistically significant (p < 0.05) from placebo

A t-test was used to determine existing differences between products (p<0.05). The enzyme dentifrice (0.226% ficin) is statistically different from the matching placebo. The ficin-containing dentifrice showed a clinical plaque reduction by an anti-adhesion mode of action.

B. Modified Gingival Margin Plaque Index Determination (MGMPI)—Test Products 0.226% Papain and Matching Negative Control This clinical procedure was identical to that described above for ficin, except for the fact that 14 panelists were enrolled in this study all of whom completed the study.

| Plaque score (MGMPI) | Enzyme toothpaste (0.226% Ficin) | Matching Placebo toothpaste |
|---|---|---|
| Mean 24 hr. score | 17.07 ± 7.03* | 30.38 ± 17.95 |

*Statistically significant (p < 0.05) from placebo

A t-test was used to determine existing differences between products (p<0.05). The enzyme dentifrice (0.226% papain) is statistically different from the matching placebo. The papain-containing dentifrice showed a clinical plaque reduction by an anti-adhesion mode of action. Comparing the results for the two clinicals, it is further concluded that ficin-containing dentifrice showed a directionally better anti-adhesion efficacy then papain-containing dentifrice.

The GMP produced batches were aged for 6 weeks at 49° C. The enzyme activity of each of the enzymes was nearly unchanged compared to the initial activity numbers.

EXAMPLE V

Dentifrice Formulation Containing Anti-adhesion Enzyme and Antibacterial Agent

The procedure of Example I above is repeated, except that the amount of water is reduced and replaced with a corresponding amount of the exemplary antibacterial agent, CPC. Accordingly, water was reduced to 16.7 weight percent and CPC was included in an amount of 0.3 weight percent for each of the three formulations, as in Table 1.

What is claimed is:

1. An oral treatment composition comprising:
   a vehicle comprising:
     a cysteine protease anti-adhesion agent and
     a mixed surfactant system comprising sodium lauryl sulfate, a block copolymer of ethylene oxide and propylene oxide and a betaine
   wherein the cysteine protease anti-adhesion agent and the mixed surfactant system are not segregated upon formulation of said oral treatment composition.

2. The composition of claim 1, wherein the anti-adhesion agent comprises at least one selected from the group consisting of ficin, papain and krillase.

3. The composition of claim 2, wherein the cysteine protease is ficin.

4. The composition of claim 1, wherein the betaine comprises cocamidopropyl betaine.

5. The composition of claim 1, further comprising an antibacterial, agent,
   wherein the antibacterial agent comprises a quaternary ammonium compound.

6. The composition of claim 5, wherein the antibacterial agent comprises an alkyl pyridinium halide.

7. The composition of claim 5, wherein the antibacterial agent comprises cetyl pyridinium chloride.

8. The composition of claim 5, wherein the antibacterial agent is cetyl pyridinium chloride and the anti-adhesion agent is ficin.

9. The composition of claim 8, wherein the betaine comprises cocamidopropyl betaine.

10. The composition of claim 5, wherein, on the basis of 100 parts by weight of the oral treatment composition, the antibacterial agent is present in an amount of at least about 0.01 parts.

11. The composition of claim 5, wherein, on the basis of 100 parts by weight of the oral treatment composition, the antibacterial agent is present in an amount of at least about 0.05 parts.

12. The composition of claim 5, wherein, on the basis of 100 parts by weight of the oral treatment composition, the antibacterial agent is present in an amount of about 0.03 to about 0.30 parts.

13. The composition of claim 1, wherein, on the basis of 100 parts by weight of the oral treatment composition, the anti-adhesion agent is present in an amount of up to about 10 parts.

14. The composition of claim 1, wherein, on the basis of 100 parts by weight of the oral treatment composition, the anti-adhesion agent is present in an amount of at least about 0.01 parts.

15. The composition of claim 1, wherein, on the basis of 100 parts by weight of the oral treatment composition, the anti-adhesion agent is present in an amount of at least about 0.05 parts.

16. The composition of claim 1, wherein, on the basis of 100 parts by weight of the oral treatment composition, the anti-adhesion agent is present in an amount of about 0.03 to about0.5 parts.

17. The composition of claim 1 wherein the mixed surfactant system comprises 0.5% sodium lauryl sulfate, 1.5% block copolymer of ethylene oxide and propylene oxide and 1% betaine.

* * * * *